United States Patent [19]
Elson

[11] Patent Number: 5,888,988
[45] Date of Patent: *Mar. 30, 1999

[54] COVALENTLY LINKED N,O-CARBOXYMETHYLCHITOSAN AND USES THEREOF

[75] Inventor: Clive M. Elson, Halifax, Canada

[73] Assignee: Chitogenics, Inc., Morristown, N.J.

[*] Notice: The term of this patent shall not extend beyond the expiration date of Pat. No. 5,679,658.

[21] Appl. No.: 852,005

[22] Filed: May 6, 1997

Related U.S. Application Data

[63] Continuation-in-part of Ser. No. 436,770, May 8, 1995, Pat. No. 5,679,658.

[51] Int. Cl.$^6$ .............................. A61K 31/73; A61F 2/00
[52] U.S. Cl. .................................... 514/55; 514/2; 514/8; 514/54; 536/20; 604/57; 424/422; 424/423; 424/424; 424/426; 424/488
[58] Field of Search .............................. 514/2, 8, 54, 55; 536/20; 604/57; 424/422, 423, 424, 426, 488

[56] References Cited

U.S. PATENT DOCUMENTS

| | | | |
|---|---|---|---|
| 4,141,973 | 2/1979 | Balazs | 424/180 |
| 4,424,346 | 1/1984 | Hall et al. | 536/20 |
| 4,619,995 | 10/1986 | Hayes | 536/20 |
| 4,819,617 | 4/1989 | Goldberg et al. | 128/897 |
| 4,886,787 | 12/1989 | deBelder et al. | 514/57 |
| 5,023,090 | 6/1991 | Levin | 424/520 |
| 5,080,893 | 1/1992 | Goldberg et al. | 514/57 |
| 5,093,319 | 3/1992 | Higham et al. | 514/55 |
| 5,140,016 | 8/1992 | Goldberg et al. | 514/57 |
| 5,411,988 | 5/1995 | Bockow et al. | 514/560 |
| 5,412,084 | 5/1995 | Elson et al. | 536/20 |
| 5,462,990 | 10/1995 | Hubbell et al. | 525/54.1 |

FOREIGN PATENT DOCUMENTS

| | | |
|---|---|---|
| 665022 | 8/1995 | European Pat. Off. . |
| WO 93/13137 | 7/1993 | WIPO . |

OTHER PUBLICATIONS

Buckman, R. et al., "A Physiologic Basis for the Adhension–free Healing of Deperitonealized Surfaces", *Journal of Surgical Research*, vol. 21, pp. 67–76 (1976);
Elikin, T. et al., "Adhension Prevention by Solutions of Sodium Carboxymethylcellulose in the rat. I", *Fertility and Sterility*, Vol. 41 (6), pp. 926–928 (Jun. 1984);
Elkins, T. et al., "Adhension Prevention by Solutions of Sodium Carboxymethylcellulose in the rat. II", *Fertility and Sterility*, vol. 41 (6), pp. 929–932 (Jun. 1984);
Fukasawa, M. et al., "Inhibition of Postsurgical Adhensions in a Standardized Rabbit Mode: II. Intraperitoneal Treatment with Heparin", *Int. J. Fertil.*, vol. 36 (50, pp. 296–301 (1991);
Gervin, A. et al., "Serosal Hypofirnolysis", *The Americal Journal of Surgery*, vol. 125, pp. 80–88 (Jan. 1973);
Hemadeh, O. et al., "Prevention of Peritoneal Adhensions by Administration of Sodium Carboxymethylcellulose and Oral Vitamin E", *Surgery*, vol. 114, pp. 907–910 (Nov. 1993);
Horano, S. et al., "Chitin and Chitosan for use as a Novel Biomedical Material", *Proceedings of the Symposium on Advances in Biomedical Polymers*, pp. 285–296, 190th National American Chemistry Society Meeting in Chicago, IL held Sept. 8–15 (1985);
Holtz, G., "Prevention of Postoperative Adhensions", *The Journal of Reproductive Medicine*, vol. 24 (4), pp. 141–146 (Apr. 1980);
Langford, M. et al., "Effects of Healon®, N, O Carboxymethyl Chitosan® and Vitreon® on Conjunctival Cells and Human Peripheral Blood Lymphocytes", *Southern Biomedical Engineering Conference–Proceedings*, IEEE, pp. 286–288 (1995);
Levinson, C. et al., "Postoperative Adhensions: Etiology, Prevention, and Therapy", *Clinical Obsteterics and Gynecology*, vol. 23 (4), pp. 1213–1220 (Dec. 1980);
Muzzarelli, R. et al., "Carboxymethylated Chitins and Chitosans", *Carbonhydrate Polymers*, vol. 8, pp. 1–21 (1988);
Nair, S. et al., "Role of Proteolytic Enzyme in the Prevention of Postoperative Intraperitoneal Adhensions", *Arch. Surg.*, vol. 108, pp. 849–853 (Jun. 1974);
Pouyiani, T. et al., "Novel Hydrogels of Hyaluronic Acis: Synthesis, Surface Morphology, and Solid–State NMR", *j. Am. Chem. Soc.*, vol. 116, pp. 7515–7522 (1994);
Rinaudo, M. et al., "Substituent Fistribution on o, N–carboxymethylchitosans by $^1$H and $^{13}$C n.m.r. ", *Int. Journal of Biol. Macromol.*, vol. 14 (3), pp. 122–128 (1992);
Sahin, Y. et al., "Synergistic Effects of Carboxymethlycellulose and Low Molecular Weight Heparin in Reduction Adhension Adhension Formation in the Rat Uterine Horn Model", *Acta Obstst. Gynecol. Scand.*, vol. 73, pp. 70–73 (1994);
Sawhney, A et al., "Optimization of Photopolymerized Bioerodible Hydrogel Properties for Adhension Prevention", *Journal of Biomedical Materials Research*, vol. 28 pp. 831–838 (1994);
Thompson, J. et al., "Reduced Human Peritoneal Plasminogen Activating Activity: Possible Mechanism of Adhension Formation", *br. J. Surg.*, vol. 76, pp. 382–384 (Apr. 1989);
Yalpani, M. et al., "Some Chemical and Analytical Aspects of Polysaacchride Modifications. $^1$3. Formation of Branched–Chain, Soluble chitosan Derivatives$^2$", *Macromolecules*, vol. 17, pp. 272–281 (1984).

*Primary Examiner*—Kathleen K. Fonda
*Attorney, Agent, or Firm*—Lahive & Cockfield, LLP

[57] ABSTRACT

Covalent compositions of N,O-carboxymethyl chitosan (NOCC) are disclosed. NOCC can be intra- or intermolecularly linked, either through a direct bond or through a bridging moiety. Also disclosed are methods for preparing and using the covalent NOCC compositions. The NOCC compositions are useful in the administration of therapeutically active compounds and for wound management.

35 Claims, No Drawings

COVALENTLY LINKED N,O-CARBOXYMETHYLCHITOSAN AND USES THEREOF

CROSS-REFERENCE TO RELATED APPLICATIONS

This application is a continuation-in-part of U.S. patent application Ser. No. 08/436,770, filed May 8, 1995, now U.S. Pat. No. 5,679,658, entitled "N,O-Carboxymethylchitosan for Prevention of Surgical Adhesions," the entire contents of which are incorporated herein by reference.

BACKGROUND OF THE INVENTION

Polymers have enjoyed increasing use in medical applications in recent years. Such polymers, which can be synthetic materials or may be derived from natural sources, have been employed for applications as diverse as delivery of therapeutic agents, e.g., drugs, in time-release formulations; reconstruction of tissue defects (for example, in plastic surgery); protection of damaged tissues; prevention of post-surgical adhesions; and the like.

Post-surgical adhesions are caused by a combination of factors including manipulative trauma and drying of the tissues during the surgery itself. A number of techniques attempting to ameliorate these problems have been described. Highly concentrated solutions of a number of polymers have been used to coat the surgical area before, and during, surgery so as to minimize the drying and act as "cushion" to prevent some of the manipulative trauma. Examples of these techniques are described in U.S. Pat. No. 4,819,617, to Goldberg et al., U.S. Pat. No. 4,886,787 to De Belder et al., and the above-referenced co-pending U.S. patent application Ser. No. 08/436,770. Among the materials used included polyvinylpyrrolidone, dextrans, carboxymethylcelluloses, and a number of other polymers such as protein or polypeptide solutions. One promising polymer which has been used is hyaluronic acid ("HA"). A series of patents by Goldberg et al., particularly U.S. Pat. No. 5,080,893 and U.S. Pat. No. 5,140,016, show the use of pretreatment of surgical sites with hyaluronic acid solutions as a means of preventing surgical adhesions.

Hyaluronic acid has several problems associated with its use. One problem with using hyaluronic acid is its cost. Hyaluronic acid can be obtained from rooster combs or human umbilical cords, and requires substantial purification to make pure enough to use in surgical techniques. See, e.g., U.S. Pat. No. 4,141,973, to Balazs, which describes methods of purifying hyaluronic acid. Hyaluronic acid can also be obtained in recombinant form, but is expensive. Even if the high cost and/or difficulties in purification can be justified, hyaluronic acid can have proteins associated with it which may cause tainting of the open surgical wound.

A variety of polymers have been employed as drug delivery systems, e.g., for slow release of therapeutic agents. Polymeric drug delivery systems generally are of two types: polymers which physically entrap a drug, and polymers to which a therapeutic agent is chemically linked. In the former case, the drug is released by gradual diffusion from the polymer matrix as the matrix breaks down or is degraded, while in the latter polymers, the drug is chemically released from the polymer. Such slow-release polymers can be administered to a subject, e.g., by injection or implantation, to provide drug therapy for a prolonged period. Slow-release polymers are convenient because depot dosing increases patient compliance with the drug regimen, reducing or eliminating the need for repeated drug administration. In addition, a slow-release polymer formulation can be implanted in a discrete organ or tissue, which in some cases provides localized therapeutic action of the released drug while decreasing systemic side effects.

Chitin, the primary building block of the shells of crustaceans and many insects, has been modified for use as a polymer in medical applications. Chitin can be obtained relatively inexpensively, primarily from waste products which might otherwise be discarded. U.S. Pat. No. 4,619,995, issued on an application by Hayes, describes a novel derivative of chitin, NOCC. NOCC has carboxymethyl substitutes on some of both the amino and hydroxyl sites of the glucosamine units of the chitosan structure and can be used in an uncrossed linked form as a solution; it can be cross-linked or complexed into a stable gel. For example, in the NOCC compositions of Hayes, the degree of substitution was typically less than one, with a distribution of hydroxyl to amino substitution of approximately 2:1. Thus, approximately 50% of the amino groups of the NOCC material of Hayes are not substituted with carboxymethyl groups (see also U.S. Pat. No. 5,412,084 to Elson et al.) Because of its advantageous physical properties, and its relative low cost compared with materials like hyaluronic acid, NOCC presents advantageous properties for use in applications such as surgical techniques.

Previously-described methods for crosslinking NOCC have, however, suffered from certain disadvantages. For example, NOCC has been covalently crosslinked through the use of bifunctional reagents such as glyoxal, in which each of the two aldehyde groups of glyoxal reacts with an amino group of NOCC, resulting in a crosslinked product (see, e.g., the above-referenced U.S. Pat. No. 4,619,995). This product includes the 2-carbon backbone of glyoxal as a covalently-bonded bridging moiety of the crosslinked adduct; this bridging moiety cannot readily be removed from the crosslinked NOCC without destroying the crosslinked NOCC. NOCC has also been ionically crosslinked, e.g., by addition of a cation such as divalent calcium, to form gels. However, ionically cross-linked NOCC gels have only moderate stability, e.g., to heat or solvents, and can dissolve in aqueous solutions.

Accordingly, it is an object of the present invention to provide covalently linked NOCC in which no bridging moiety is present.

It is a further object of the invention to provide a derivative of NOCC in which a therapeutic agent is releasably bound to, or entrapped by, NOCC, to provide a sustained release compound comprising NOCC and a therapeutic agent.

It is a further object of the invention to provide crosslinked NOCC in which linking occurs through a bond between a carboxyl group of a N,O-carboxymethylchitosan chain and an amino group of a N,O-carboxymethylchitosan chain.

It is still a further object of the invention to provide methods for wound management by administering linked NOCC to a subject.

It is another object of the invention to provide methods for preventing post-surgical adhesions by administering linked NOCC to a subject.

It is yet a further object of the invention to provide methods for administering a therapeutic agent to a subject by administering to the subject a composition comprising NOCC and a therapeutic agent.

These and other objects, features, and advantages of the invention will be apparent from the following description and claims.

SUMMARY OF THE INVENTION

The invention provides novel compositions of NOCC, methods of making such compositions, and methods of use for NOCC compositions.

Definitions

As used herein, the term "linking" refers to the process of forming a covalent bond between two reactive functional groups or moieties (e.g., two functional groups of NOCC, or a functional group of NOCC and a functional group of an active agent), e.g., an amino group and a carboxyl group. Linking can be accomplished by use of a coupling reagent, which promotes reaction of two reactive functional groups with each other to form a direct bond, or with a cross-linking reagent, which modifies at least one of the functional groups before reaction with the other functional group, and results in the incorporation of a bridging moiety in the covalently linked product. Linking can occur between two functional groups of a single NOCC chain (intramolecular linking), between functional groups of two NOCC chains or between a NOCC chain and an active agent (both forms of intermolecular linking).

For example, a carboxyl group and an amino group can react through use of a coupling reagent such as a carbodiimide, e.g., dicyclohexylcarbodiimide (DCC). DCC-promoted reaction results in the formation of an amide bond directly between the amino group and the carboxyl group, i.e., by a dehydration reaction. Many carbodiimide coupling reagents are known to the ordinarily skilled artisan, and many are commercially available. Examples include DCC, 1-ethyl-3-(3-dimethylaminopropyl)-carbodiimide (EDC) (both available from, e.g., Aldrich Chemical, Milwaukee, Wis.), and the like. Other coupling agents are known which may find use in the present invention. For example, a variety of agents are known, e.g., for coupling of amino acids. Exemplary coupling reagents include BOP, HBTU, TBTU, TOPPipU, PyBOP, and BOP-Cl (see, e.g., G. A. Grant, Ed., "Synthetic Peptides: A User's Guide", W. H. Freeman, New York (1992), Chp.3, and M. Bodansky, "Principles of Peptide Synthesis", 2nd ed., Spring-Verlag (1993), the entire contents of which are hereby incorporated by reference).

The term "intermolecular linking," as used herein, refers to linking between two chemical compounds, rather than intramolecular linking within one molecule. Thus, linking of NOCC to an active agent, or linking of one chain of NOCC to a second chain of NOCC, is referred to herein as intermolecular linking. When NOCC is linked to an active agent, the NOCC-active agent product is referred to herein as a "NOCC-active agent adduct."

Use of a "bridging reagent", as that term is used herein, results in the formation of a covalent linkage between the two functional groups, which linkage incorporates a linking or bridging moiety. Thus, the amino group of an amino acid can react with a carboxyl group of NOCC (to form a first amide bond), and the remaining carboxyl group of the amino acid can react with an amino group of NOCC (forming a second amide bond). Thus, a covalent bridging linkage can be formed between two functional groups of NOCC, with an amino acid moiety bridging intermediate the two NOCC functional groups. The two reactions of a bridging reagent need not be simultaneous; for example, an amino acid bearing a blocking group on the carboxyl functionality can be linked to NOCC (by reaction of a carboxyl group of NOCC with the free amino group of the amino acid), and the blocking group can then be removed, to reveal a carboxyl moiety of the amino acid, which is then capable of reaction with an amino group of NOCC. For examples of bridging reagents, see, e.g., S. S. Wong, "Chemistry of Protein Conjugation and Cross-Linking," CRC Press (1991), and G. T. Hermanson, "Bioconjugate Techniques," Academic Press (1995).

It will be appreciated by the skilled artisan that the two reactive functional groups to be linked can be different (e.g., an amino group and a carboxyl group) or can be the same (e.g., two amino groups). For linking two different functional groups, either coupling reagents or cross-linking (bridging) reagents can be employed, whereas when the functional groups are the same, a bridging reagent is generally preferred.

The terms "patient" or "subject," as used herein, refer to an animal, preferably a warm-blooded animal such as a mammal, including cattle, sheep, pigs, horses, dogs, cats, and humans.

The terms "therapeutically active agent" or "active agent," as used herein, refer to compounds which have known therapeutic utility in a subject. Therapeutically active agents include drugs such as antibiotics, anti-inflammatories, antihypertensives, cholesterol-lowering drugs, anti-neoplastics, and the like. Therapeutically active agents include synthetic and naturally-occurring compounds, which can be, e.g., proteins, peptides, carbohydrates, small molecules, and the like. Active agents can be active free in solution and/or when linked to NOCC as described herein. If an active agent is active only in the free state, it is preferably linked to NOCC through a cleavable covalent bond.

The term "wound management," is known in the art and, as used herein, refers to treatments for improving or promoting healing of wounds, including debridement of wounds, prevention or minimization of infection and inflammation, topical application of active agents to wounds, absorption of exudate fluid, moisturization of wounds, wound dressing, and the like.

In one aspect, the invention provides linked N,O-carboxymethylchitosan, wherein linking occurs through a bond between a carboxyl group of a N,O-carboxymethylchitosan chain and an amino group of a N,O-carboxymethylchitosan chain.

The bond which links a carboxyl group and an amino group can be an amide bond, for example, an amide bond which links an O-carboxymethyl group (e.g., a 3- or 6-carboxymethyl group), or an N-carboxymethyl group, of a N,O-carboxymethylchitosan chain with a 2-amino group of a N,O-carboxymethylchitosan chain. The covalently linked NOCC can be in the form of a hydrogel, or in a dehydrated form which absorbs 50 or more times its weight of liquid, which can entrap an active agent, such as a therapeutically active compound. Intermolecular linking can occur through a bond between a carboxyl group of a first N,O-carboxymethylchitosan chain and an amino group of a second N,O-carboxymethylchitosan chain, and intermolecular linked NOCC can have an average molecular weight of at least about 500,000 daltons. Linking can occur through a direct amide bond between a carboxyl group of the first N,O-carboxymethylchitosan chain and an amino group of the second N,O-carboxymethylchitosan chain, or the first and second N,O-carboxymethylchitosan chains can be linked by a bridging moiety. In certain applications, the linking is intramolecular.

In another aspect, the invention provides a method for preparing linked N,O-carboxymethylchitosan. The method includes the step of reacting N,O-carboxymethylchitosan in the presence of a coupling reagent under conditions such that an amino group of a N,O-carboxymethylchitosan chain forms a direct amide bond with a carboxyl group of a N,O-carboxymethylchitosan chain, thereby preparing directly linked N,O-carboxymethylchitosan. The coupling reagent can be a reagent such as a carbodiimide, or a coupling reagent selected from the group consisting of BOP, HBTU, TBTU, TOPPipU, PyBOP, and BOP-Cl. The method can optionally include the use of a catalyst which promotes amide bond formation, such as N-hydroxysuccinimide or HOBt.

In another aspect, the invention provides a method for directly linking an active agent to N,O-carboxymethylchitosan, i.e., to form NOCC-active agent adduct. The method includes reacting N,O-carboxymethylchitosan and the active agent in the presence of a coupling reagent, under conditions such that a direct covalent bond is formed between the N,O-carboxymethylchitosan and the active agent, thereby directly intermolecularly linking the active agent to N,O-carboxymethylchitosan to form a NOCC-active agent adduct. As with the NOCC compounds described above, the covalent bond can be an amide bond; preferably, but optionally, the covalent bond is hydrolyzable, i.e., can be hydrolyzed, preferably under physiological conditions, through either enzymatic or non-enzymatic processes. A carboxyl group of the active agent can react with an amino group of N,O-carboxymethylchitosan to form the amide bond, which can be a direct bond between a carboxyl group of the active agent and an amino group of a N,O-carboxymethylchitosan chain. Alternatively, an amino group of the active agent can react with a carboxyl group of N,O-carboxymethylchitosan to form the amide bond, which can be a direct bond between an amino group of the active agent and an carboxyl group of a N,O-carboxymethylchitosan chain. The active agent can be any agent which can react with NOCC, including proteins and peptides. In some embodiments, the N,O-carboxymethylchitosan linked to the active agent is itself intra- or intermolecularly linked N,O-carboxymethylchitosan. The active agent can be a therapeutically-active compound.

In still another aspect, the invention provides a compound comprising N,O-carboxymethylchitosan linked to an active agent (i.e., a NOCC-active agent adduct); or a pharmaceutically-acceptable salt thereof, wherein the NOCC is linked to the active agent through an amide bond. The composition can further include a pharmaceutically-acceptable carrier. The N,O-carboxymethylchitosan moiety can be linked to the active agent directly or through a bridging moiety.

In yet another aspect, the invention provides a method for administering a therapeutically-effective compound to a patient. The method includes applying a covalent adduct of N,O-carboxymethylchitosan and a therapeutically-effective compound, or a pharmaceutically-acceptable salt thereof, in a pharmaceutically-acceptable carrier, to the patient under conditions such that the therapeutically-effective compound is administered to the patient.

Further, the invention provides a method for minimizing post-surgical adhesions. The method includes the step of applying an effective amount of covalently linked N,O-carboxymethylchitosan, or a pharmaceutically-acceptable salt thereof to tissue under conditions such that post-surgical adhesions are minimized.

The invention also provides methods for wound management. The method includes the step of applying an effective amount of covalently linked N,O-carboxymethylchitosan, or a pharmaceutically-acceptable salt thereof to a wound under conditions such that wound healing is promoted.

In still another aspect, the invention provides intermolecularly bridged N,O-carboxymethylchitosan, wherein bridging occurs through a bond between a carboxyl group of a first N,O-carboxymethylchitosan chain and a carboxyl group of a second N,O-carboxymethylchitosan chain.

In another aspect, the invention provides intermolecularly bridged N,O-carboxymethylchitosan, wherein bridging occurs through an amide bond between amino groups on first and second N,O-carboxymethylchitosan chains, wherein the amino groups are linked by a bridging moiety.

DETAILED DESCRIPTION OF THE INVENTION

The invention pertains to covalently linked NOCC, NOCC which is covalently linked to a therapeutic agent, methods for making the novel compositions, and to methods for treating a subject by administration of the novel NOCC compositions of the invention.

I. Compounds

In one aspect, the invention provides covalently linked N,O-carboxymethylchitosan, wherein linking occurs through a bond between a carboxyl group of a N,O-carboxymethylchitosan chain and an amino group of a N,O-carboxymethylchitosan chain. The invention also provides pharmaceutically acceptable salts of the covalently-linked NOCC. The compositions can further include a pharmaceutically acceptable carrier. The covalent linking can be accomplished through the use of a coupling reagent or bridging reagent, as described herein. The linking can be intramolecular (between amino and carboxyl groups of a single NOCC chain) or intermolecular (between amino and carboxyl groups of different NOCC chains).

The preferred bond is an amide bond. Thus, for example, use of a coupling reagent such as a carbodiimide results in direct linking of an amino group of NOCC to a carboxyl group of NOCC, to form a direct amide bond. However, a bridging moiety can also be employed. For example, an amino group of NOCC can be directly linked (intermolecularly) to a carboxyl moiety of an amino acid; the amino group of the amino acid can then be directly linked to a carboxyl group of NOCC (which may be on the same NOCC chain or a different NOCC chain) to provide an amino group of NOCC linked to a carboxyl group of NOCC through an amide bond (or more than one amide bond) which includes a bridging moiety (in this example, an amino acid backbone). The amide bond preferably links a 3- or 6-carboxymethyl group, or an N-carboxymethyl group, of a N,O-carboxymethylchitosan chain, with a 2-amino group of a N,O-carboxymethylchitosan chain.

Advantageously, the covalently linked NOCC can be in the form of a gel, including a hydrogel. As described in the Examples, infra, linking of NOCC with a coupling reagent readily produces gels. Such gels can be easily handled and applied to, e.g., wounds or surgical sites, for therapeutic purposes, such as wound management or the inhibition of surgical adhesions. According to one practice of the invention, the gel entraps an active agent, e.g., a therapeutically active compound such as a drug. In this embodiment, the covalently linked NOCC serves as a carrier for the therapeutically active agent, to provide sustained release or activity of the agent. The therapeutically active agent is physically entrapped within the gel matrix, and can escape by diffusion through the gel pores, or can be released by physical or chemical degradation of the gel structure.

Intermolecular linking can occur through a bond between a carboxyl group of a first N,O-carboxymethylchitosan chain and an amino group of a second N,O- carboxymethylchitosan chain. The resulting intermolecularly linked NOCC derivative generally has a molecular weight greater than the average molecular weight of the individual NOCC chains used in the linking reaction. For example, the intermolecularly linked NOCC can have an average molecular weight of at least about 500,000 daltons. Linking can occur through a direct amide bond between a carboxyl group of the first NOCC chain and an amino group of the NOCC chain. In certain instances, the first and second NOCC chains can be linked by a bridging moiety.

The linking can also be intramolecular (i.e., between functional groups of a single NOCC chain). The average molecular weight of such intramolecularly linked NOCC is not significantly different from the average molecular weight of the unlinked NOCC, although the apparent molecular weight, as measured by techniques such as gel filtration, may appear different due to changes in the molecular size or shape which accompany the linking process. It will be appreciated that a given NOCC chain can be both intramolecularly linked and intermolecularly linked. Intramolecularly linked NOCC can also be linked to an active agent, to form a NOCC-active agent adduct.

In another aspect, the invention provides a compound comprising N,O-carboxymethylchitosan covalently linked to an active agent (to form a NOCC-active agent adduct), or a pharmaceutically-acceptable salt thereof. The N,O-carboxymethylchitosan can optionally be linked to the active agent through an amide bond. The N,O-carboxymethylchitosan group can be covalently linked to the active agent through a bridging moiety, or the NOCC can be directly linked to the active agent without a bridging moiety. Intermolecularly linked compounds, with or without a bridging moiety, can be prepared by intermolecular linking of the active agent with NOCC, as described in more detail infra.

The active agent can be linked to NOCC such that it can be released from the NOCC in therapeutically active form. Thus, for example, a therapeutically active compound can be linked to NOCC through a bond which can be hydrolyzed in vivo, either enzymatically or non-enzymatically. For example, certain amide bonds can be hydrolyzed by enzymes such as proteases. (For examples of other bonds which can be cleaved in vivo, see, e.g., R. B. Silverman, "The Organic Chemistry of Drug Design and Drug Action," (1992), Chp. 8, Academic Press.) Thus, the invention provides a NOCC-active agent adduct which can release the active agent through chemical cleavage of the covalent bond between NOCC and the active agent. For administration to a patient, the composition can also include a pharmaceutically-acceptable carrier.

In still another aspect, the invention provides intermolecularly bridged N,O-carboxymethylchitosan, wherein bridging occurs through a bond between a carboxyl group of a first N,O-carboxymethylchitosan chain and a carboxyl group of a second N,O-carboxymethylchitosan chain.

In another aspect, the invention provides intermolecularly bridged N,O-carboxymethylchitosan, wherein linking occurs through an amide bond between amino groups on first and second N,O-carboxymethylchitosan chains, wherein the amino groups are linked by a bridging moiety. Thus, for example, a dicarboxylic acid, such as succinic acid, can be employed as a bifunctional bridging reagent between two NOCC amino groups, such that the resulting bridged NOCC is linked through at least one (or in this example, two) amide bonds. Such bridging can be accomplished by reaction of NOCC with, e.g., succinic anhydride, to provide succinylated NOCC; the succinic carboxylate moieties can then be directly linked to amino groups of a second NOCC chain (preferably in the presence of a coupling reagent) to provide bridged NOCC in which bridging occurs through an amide bond between amino groups on the first and second NOCC chains.

II. Methods

In another aspect, the invention provides a method for preparing covalently linked N,O-carboxymethylchitosan. The method includes the step of reacting N,O-carboxymethylchitosan in the presence of a coupling reagent under conditions such that an amino group of a N,O-carboxymethylchitosan chain forms an amide bond with a carboxyl group of a N,O-carboxymethylchitosan chain, thereby preparing covalently linked N,O-carboxymethylchitosan.

The use of coupling reagents to promote reaction of an amino group with a carboxyl group to form an amide bond is well known, and a variety of coupling reagents and procedures are available for this purpose (see, e.g., G. A. Grant, Ed., "Synthetic Peptides: A User's Guide", supra, and M. Bodansky, "Principles of Peptide Synthesis", supra). The coupling reagent can be a carbodiimide, such as DCC, EDC, and the like; or the coupling reagent can be selected from other reagents, such as BOP, HBTU, TBTU, TOPPipU, PyBOP, and BOP-Cl. Optionally, the method can include the use of a catalyst which promotes amide bond formation. Exemplary catalysts include N-hydroxysuccinimide and HOBt. Linking reactions can be performed in a variety of solvents, although the limited solubility of NOCC in many organic solvents will generally require that the solvent be water or an aqueous mixture. It will be appreciated that both intramolecular and intermolecular linking can occur in solutions of NOCC. The amount of intramolecular product formed compared to the amount of intermolecularly linked product can be altered by factors such as dilution (dilute solutions generally favor intramolecular reaction), the presence of other agents which can react with NOCC, and the like.

In another aspect, the invention provides a method for intermolecularly linking an active agent to N,O-carboxymethylchitosan to form a NOCC-active agent adduct. The method includes reacting N,O-carboxymethylchitosan and the active agent in the presence of a coupling reagent, under conditions such that a direct bond is formed between the N,O-carboxymethylchitosan and the active agent, thereby (intermolecularly) directly linking the active agent to N,O-carboxymethylchitosan to form a NOCC-active agent adduct. The direct bond can be an amide bond, or, in some instances, can be a bond such as an ester or thioester. If a therapeutically active agent is linked to NOCC, it can be advantageous for the direct bond to be capable of hydrolysis (or other cleavage, such as oxidation or reduction) under conditions found in vivo. Thus, the agent can be cleaved from NOCC after administration to a patient, for example by an enzyme, releasing the therapeutically-active compound.

A carboxyl group of the active agent can react with an amino group of N,O-carboxymethylchitosan to form an amide bond, which can be a direct bond between a carboxyl group of the active agent and an amino group of a N,O-carboxymethylchitosan chain. Alternatively, an amino group of the active agent can react with a carboxyl group of N,O-carboxymethylchitosan to form an amide bond, which can be a direct bond between an amino group of the active agent and an carboxyl group of a N,O-carboxymethylchitosan chain. The active agent is preferably a therapeutically-active compound. Any active agent which includes a functional group capable of reaction with NOCC, or with a bridging group linked to NOCC, can be employed. For example, the active agent can be a protein or peptide, which can be linked to NOCC in a variety of ways, including direct linking (e.g., through the terminal amine or terminal carboxyl group of a protein, or through a reactive group of a side chain, such as an amine, a carboxyl group, a hydroxyl group, or a thiol group, of a protein). The N,O-carboxymethylchitosan can be inter- or intramolecularly linked N,O-carboxymethylchitosan.

Linking of an active agent to NOCC in the presence of a coupling reagent can also result in intramolecular or intermolecular direct linking of NOCC, as described supra. Formation of the NOCC-active agent adduct can be favored by, e.g., use of protecting groups to temporarily block reactive groups of NOCC. For example, the amino groups of NOCC can be temporarily blocked with an amine protecting group, leaving the carboxyl groups of NOCC unprotected. The protected NOCC can then be directly linked with an amine-containing active agent, in the presence of a coupling reagent, without excessive intra- or intermolecular linking of NOCC. When formation of the protected NOCC-active agent adduct is complete, the amine-protecting groups on the NOCC chain can be removed to provide the NOCC-active agent adduct. Similarly, the carboxyl groups of NOCC can be blocked when direct linking to a carboxyl-containing active agent is desired. (For a general reference to protecting groups, see, e.g., T. W. Greene and P. G. M. Wuts, "Protective Groups in Organic Synthesis," 2nd Ed., John Wiley & Sons (1991).)

In yet another aspect, the invention provides a method for administering a therapeutically-effective compound to a patient. The method includes applying a NOCC-active agent adduct, or a pharmaceutically-acceptable salt thereof, optionally in a pharmaceutically-acceptable carrier, to the patient under conditions such that the therapeutically-effective compound is administered to the patient. The therapeutically-effective compound can be released by cleavage of the covalent bond to NOCC, as described supra. The covalently linked compounds of NOCC with a therapeutically active agent can be prepared as described herein. Where the NOCC-active agent adduct is in the form of a gel, the gel can be administered directly. The adduct can also be dissolved or suspended in a pharmaceutically acceptable carrier for administration by other routes which are conventional in the art.

In still another aspect, the invention provides a method for minimizing post-surgical adhesions. The method includes the step of applying an effective amount of covalently linked N,O-carboxymethylchitosan, or a pharmaceutically-acceptable salt thereof to tissue under conditions such that post-surgical adhesions are minimized. Examples of the administration of NOCC gels for prevention of post-surgical adhesions are described in more detail in co-pending U.S. patent application Ser. No. 08/436,770.

The invention also provides methods for wound management, e.g., debridement of wounds, prevention or minimization of infection and inflammation, topical application of active agents to wounds, absorption of exudate fluid, moisturization of wounds, wound dressing, and the like. The method includes the step of applying an effective amount of covalently linked N,O-carboxymethylchitosan, or a pharmaceutically acceptable salt thereof, to a wound under conditions such that the wound is managed, i.e., such that wound healing is promoted. It will be appreciated that the covalently linked NOCC can be in the form of a gel (e.g., a hydrogel) or in the form of a solid, e.g., a dried solid, provided that the NOCC composition is capable of absorbing substantial amounts of liquid exudate from the wound. Advantageously, a linked NOCC composition of the invention, when applied in dry form, can absorb at least about 50 times its dry weight in liquid, and, in certain embodiments, can absorb up to 500 times its weight in liquid. It will also be appreciated that wound management according to the methods of the invention can include combinations of two or more of the wound management modalities described herein, e.g., covalently linked NOCC to which an active agent has been linked can be applied to a wound both to absorb exudate and to provide a sustained-release formulation of the active agent to promote wound healing, thereby promoting wound healing through a combination of mechanisms.

EXEMPLIFICATION

Example 1

Carbodiimide-mediated Linking of NOCC

Dry NOCC (2.0 g) was added to solution of deionized water (200 ml) and a small amount of sodium chloride (0.5 g), and stirred for approximately 30 mins. A minimum of heat was applied to ensure the polymer was properly dissolved. The pH of the solution was adjusted to measure between seven and eight. If the pH measured above eight, dilute hydrochloric acid was added to the solution to lower the pH to between seven and eight. Addition of acid sometimes caused partial precipitation of NOCC, in which case the mixture was stirred until the NOCC was again fully dissolved (generally a minimum of 3 hrs). The carbodiimide EDC (1-ethyl-3-(3-dimethylaminopropyl)-carbodiimide) was dissolved in 5–7 milliliters of water and the pH of the EDC solution was adjusted to measure between seven and eight. The EDC solution was then added to the NOCC solution dropwise with vigorous stirring. N-hydroxysuccinimide (NHS) was dissolved in water (3–5 ml), the pH was adjusted to between seven and eight as above, and the NHS solution was added to the NOCC/EDC mixture, preferably within 2–3 mins of the EDC addition. The solution was allowed to stir for an additional 15 mins, or until the solution gelled, thereby preventing the stirbar from spinning. If the gel set quickly and stirring was impaired, the gelatinous substance was stirred with a spatula to ensure proper mixing. The stirbar was removed with a retriever and the beaker was covered with parafilm. The reaction mixture was permitted to stand overnight at ambient temperature and had an average curing time of eighteen hours. The procedure remained the same for all preparations, varying only the molar ratios of EDC and NHS. Throughout the experiments, the solution was stirred rapidly and any additions were made slowly, to prevent the formation of any areas of high concentration of reagents. The mole ratio of reagents used in the linking reactions are given in Table 1.

TABLE 1

| Molar Ratio NOCC:EDC:NHS | Moles of EDC | Moles of NHS |
|---|---|---|
| 10:1 | $8.86 \times 10^4$ | — |
| 5:1 | $1.83 \times 10^{-3}$ | — |
| 3:1 | $2.96 \times 10^{-3}$ | — |
| 1:1 | $9.02 \times 10^{-3}$ | — |
| 30:1:0.04 | $3.03 \times 10^{-4}$ | $8.69 \times 10^{-6}$ |
| 10:1:0.04 | $8.86 \times 10^{-4}$ | $3.48 \times 10^{-5}$ |
| 5:1:0.04 | $1.83 \times 10^{-3}$ | $6.95 \times 10^{-5}$ |
| 5:1:0.20 | $1.83 \times 10^{-3}$ | $3.65 \times 10^{-3}$ |
| 3:1:0.04 | $2.97 \times 10^{-3}$ | $1.23 \times 10^{-4}$ |

TABLE 1-continued

| Molar Ratio NOCC:EDC:NHS | Moles of EDC | Moles of NHS |
|---|---|---|
| 1:1:0.04 | $9.02 \times 10^{-3}$ | $3.65 \times 10^{-3}$ |
| 1:2:0.04 | $1.80 \times 10^{-2}$ | $7.21 \times 10^{-4}$ |

It was found that the order of addition of the various reaction components (e.g., addition of EDC to NOCC, then addition of NHS to NOCC, or vice versa) had little effect on the yield or purity of the product. When the mole ratio of EDC to NOCC was relatively high, the reaction proceeded rapidly, and the reaction mixture in some instances became so viscous that proper mixing of additional reagents (such as NHS) was difficult.

When solutions of NOCC were reacted with EDC and NHS, the viscosity increased noticeably within fifteen minutes and the solution remained clear. After 30 mins to 3 hours, depending on the level of EDC added (the gel set more quickly with increased EDC), the solution was no longer pourable and a transparent, clear gel (a hydrogel) was formed. The reaction produced a gelatinous, form-filling hydrogel which, when removed from a reaction vessel, retain its shape and was a firm hydrogel-like substance. No excess bulk water remained when the hydrogel was set, and the hydrogel generally did not release water upon standing for several days.

While the direct linking reaction proceeded in the absence of NHS, no significant reaction occurred in the absence of carbodiimide. However, NHS is a catalyst for carbodiimide-mediated reactions, and was found to significantly increase the rate of the linking reaction. For example, at certain low molar ratios of EDC:NOCC, and no NHS, the prepared gels would take up to 12 hours to set firmly; this time was often reduced to 5–6 hrs when NHS was present in the reaction mixture. Gels prepared with high molar ratios of EDC:NOCC and no NHS, set in as little as 35 mins, which was reduced to 10–15 mins in the presence of NHS. The average yields (~80%) were the same with or without NHS. Thus, NHS altered the rate of reaction but did not increase the yield.

Without wishing to be bound by theory, it is believed that the carbodiimide-mediated linking reaction of NOCC occurs by a mechanism similar to the generally accepted mechanism for carbodiimide-mediated linking. The addition of NHS is believed to promote rapid reaction by converting the O-acylurea intermediate (formed by reaction of a carboxylate group of NOCC with the carbodiimide) to an activated NHS ester, which then reacts with an amino group of NOCC to form the intermolecularly linked product.

After the reaction had proceeded for the desired time, the product was isolated. In general, the product was in the form of an extremely hydrophilic, non-soluble, clear hydrogel. The hydrogel, consisting of 2.0 g of NOCC in 200 ml of water, was purified and reduced to a solid for analysis. Initially, the hydrogel was divided into four equal portions that were individually mixed in a blender with approximately 200 ml of a 50:50 mixture of acetone and isopropanol at low speed. A white flaky precipitate was formed which was then filtered and freeze dried. The isolation procedure could be modified to include a step that would remove any salts (NaCl), byproducts (urea), or left over reagents (EDC, NHS). To remove these impurities, the hydrogel was allowed to swell in a large beaker of deionized water (300–500 ml) and then placed in dialysis tubing. The full dialysis tubes were soaked in deionized water for five to seven days, changing the water twice daily. Once the swollen hydrogel was removed from the tubing, it was dehydrated by soaking in a 50:50 mixture of acetone and isopropanol (2.0 L). A white spongy precipitate formed which was then freeze-dried. For this procedure, the use of the blender was found to be unnecessary; a precipitate was obtained by soaking the hydrogel in the 50:50 acetone:isopropanol mixture for 24 hrs, then filtering the hydrogel through a buchner funnel and returning it to a fresh acetone:isopropanol mixture for another 2–3 days. The white spongy product was then freeze dried. The final product was a white solid which was crushed using a mortar and pestle, and then passed though a fine sieve (300 $\mu$m) for further analysis.

The purified solid product was analyzed and the results were consistent with intra-and/or intermolecularly linked NOCC.

Example 2
Swelling of Direct-Linked NOCC Gels

Two different types of swelling experiments were performed on the directly linked gel products of Example 1, to determine the ability of hydrogels to absorb water. The first swelling experiment involved determining the amount of water that was absorbed by the hydrogel form (i.e., before isolation and purification). The hydrogel products of the linking reactions were allowed to swell in an excess of deionized water overnight, taking note of the volume of water added. The supernatant water was then filtered off and measured, thereby determining the amount of water absorbed by the hydrogel.

In a second experiment, 0.4 g of isolated and purified solid product (0.40 g) was allowed to swell in deionized water (500 ml). The swollen product was filtered off and the amount of water absorbed was determined. Products with varying mole ratios of NOCC, EDC and NHS were used.

As the ratio of EDC to NOCC was increased, the amount of water absorbed by the hydrogel decreased, suggesting that the hydrogel was less polar due to the extensive intermolecular linking, or that the pore size of the hydrogel was smaller, rendering the hydrogel less permeable or less able to expand to retain water. Indeed, at the highest ratio of EDC to NOCC employed, the hydrogel actually released a small amount of water. The isolated, dried linking products were also found to absorb less water when higher ratios of EDC to NOCC were employed. It was found that the isolated, dried product could absorb 50 times its weight in water when a NOCC:EDC:NHS ratio of 1:1:0.04 was used for linking, but the dried product could absorb more than 500 times its weight in water when a NOCC:EDC:NHS ratio of 10:1:0.04 was used for linking.

It was also noted that exposure to high temperature (e.g., by heating in an autoclave) resulted in some loss of rigidity of the hydrogel.

Example 3
Direct Linking of Agents to NOCC

A modified version of the procedure of Example 1 was used for the addition of agents to NOCC. Dry NOCC (2.0 g) was dissolved in 200 ml of deionized water, NaCl (0.5 g) was added, and the solution was well stirred. The pH was adjusted to between seven and eight. If the pH was above eight, some dilute hydrochloric acid was added and well stirred to redissolve any NOCC that may have precipitated out of solution. To this solution, the agent was added (in this example, butylamine and cysteine were employed), well stirred, and the desired amounts of EDC and NHS were added to the reaction mixture. For the reaction with the amino acid cysteine, the EDC and cysteine were mixed together in 50 ml of PBS buffer and the NOCC was dissolved in 150 ml buffer. The two solutions were then mixed and the NHS reagent was added. The reactions were performed at a pH at which the amino groups of butylamine and cysteine are largely protonated.

The agent to be linked to NOCC was provided in molar excess to minimize intramolecular direct linking of the NOCC. Indeed, reaction with butylamine or cysteine did not, under the conditions employed, produce a hydrogel similar to the hydrogels of Example 1. Rather, the reaction mixtures remained as viscous solutions, suggesting that intra- or intermolecular linking of NOCC had not occurred to the extent seen in the reactions of Example 1.

It was found that use of high mole ratios of NOCC:EDC in the reactions provided the most easily characterized products. Elemental analysis of the butylamine:NOCC reaction product was consistent with formation of a NOCC:butylamine linked product. Elemental analysis of the NOCC:cysteine linked product demonstrated the presence of sulfur in the linked product. Thus, the expected linking reaction between cysteine and NOCC occurred even in the presence of phosphate in the buffer.

Those skilled in the art will recognize, or be able to ascertain using no more than routine experimentation, numerous equivalents to the specific procedures described herein. Such equivalents are considered to be within the scope of this invention and are covered by the following claims.

The contents of all publications and patent applications cited herein are hereby incorporated by reference.

Other embodiments are within the following claims.

What is claimed is:

1. Linked N,O-carboxymethylchitosan, wherein linking occurs through an amide linkage between a carboxyl group of a N,O-carboxymethylchitosan chain and an amino group of a N,O-carboxymethylchitosan chain.

2. The linked N,O-carboxymethylchitosan of claim 1, wherein the amide linkage directly links a 3-, 6-, or N-carboxymethyl group of a N,O-carboxymethylchitosan chain with a 2-amino group of a N,O-carboxymethylchitosan chain.

3. The linked N,O-carboxymethylchitosan of claim 1, wherein the covalently linked NOCC is in the form of a hydrogel.

4. The linked N,O-carboxymethylchitosan of claim 3, wherein the hydrogel entraps an active agent.

5. The linked N,O-carboxymethylchitosan of claim 4, wherein the active agent is a therapeutically active compound.

6. The linked N,O-carboxymethylchitosan of claim 1, further comprising an active agent linked to the N,O-carboxymethylchitosan.

7. The linked N,O-carboxymethylchitosan of claim 1, wherein the N,O-carboxymethylchitosan is intermolecularly linked, said intermolecular linking occurring through an amide linkage between a carboxyl group of a first N,O-carboxymethylchitosan chain and an amino group of a second N,O-carboxymethylchitosan chain.

8. The intermolecularly linked N,O-carboxymethylchitosan of claim 7, wherein the intermolecularly covalently linked NOCC has an average molecular weight of at least about 500,000 daltons.

9. The intermolecularly linked N,O-carboxymethylchitosan of claim 7, wherein linking occurs through a direct amide linkage between a carboxyl group of the first N,O-carboxymethylchitosan chain and an amino group of the second N,O-carboxymethylchitosan chain.

10. The intermolecularly linked N,O-carboxymethylchitosan of claim 7, wherein the first and second N,O-carboxymethylchitosan chains are linked by a bridging moiety.

11. The linked N,O-carboxymethylchitosan of claim 1, wherein the linking is intramolecular.

12. A method for preparing linked N,O-carboxymethylchitosan, comprising:
    reacting N,O-carboxymethylchitosan in the presence of a coupling reagent under conditions such that an amino group of a N,O-carboxymethylchitosan chain forms a direct amide linkage with a carboxyl group of a N,O-carboxymethylchitosan chain thereby preparing covalently linked N,O-carboxymethylchitosan.

13. The method of claim 12, wherein the coupling reagent is a carbodiimide.

14. The method of claim 12, wherein the coupling reagent is selected from the group consisting of BOP, HBTU, TBTU, TOPPipU, PyBOP, and BOP-Cl.

15. The method of claim 12, further comprising a catalyst which promotes amide linkage formation.

16. The method of claim 15, wherein the catalyst is N-hydroxysuccinimide.

17. The method of claim 15, wherein the catalyst is HOBt.

18. A method for intermolecularly linking an active agent to N,O-carboxymethylchitosan to form a NOCC-active agent adduct, comprising
    reacting N,O-carboxymethylchitosan and the active agent in the presence of a coupling reagent, under conditions such that a direct covalent bond is formed between the N,O-carboxymethylchitosan and the active agent, thereby intermolecularly covalently linking the active agent to N,O-carboxymethylchitosan to form a NOCC-active agent adduct.

19. The method of claim 18, wherein the covalent bond is an amide linkage.

20. The method of claim 18, wherein the covalent bond can be metabolically hydrolyzed.

21. The method of claim 19, wherein a carboxyl group of the active agent reacts with an amino group of N,O-carboxymethylchitosan to form a direct amide linkage.

22. The method of claim 19, wherein an amino group of the active agent reacts with a carboxyl group of N,O-carboxymethylchitosan to form a direct amide linkage.

23. The method of claim 18, wherein the active agent is selected from the group consisting of proteins and peptides.

24. The method of claim 18, wherein the N,O-carboxymethylchitosan is linked N,O-carboxymethylchitosan.

25. The method of claim 18, wherein the active agent is a therapeutically-active compound.

26. A compound comprising N,O-carboxymethylchitosan covalently linked to an active agent, or a pharmaceutically-acceptable salt thereof, wherein the N,O-carboxymethylchitosan is linked to the active agent through an amide linkage.

27. The composition of claim 26, further comprising a pharmaceutically-acceptable carrier.

28. The compound of claim 26, wherein the N,O-carboxymethylchitosan group is covalently linked to the active agent through a bridging moiety.

29. The therapeutically active compound of claim 26, wherein the N,O-carboxymethylchitosan group is directly linked to the active agent.

30. A method for administering a therapeutically-effective compound to a patient in need thereof, the method comprising:

applying a NOCC-active agent adduct, or a pharmaceutically-acceptable salt thereof, in a pharmaceutically-acceptable carrier, to the patient under conditions such that the active agent is administered to the patient.

31. A method for wound management, the method comprising the step of applying an effective amount of the linked N,O-carboxymethylchitosan of claim 1, or a pharmaceutically-acceptable salt thereof, to a wound under conditions such that the wound is managed.

32. The method of claim 31, wherein wound management includes at least one of debridement of the wound, reducing the amount of infection, application of an active agent to the wound, absorption of exudate fluid, and moisturization of the wound.

33. A method for reducing the amount of post-surgical adhesions comprising the step of applying an effective amount of the linked N,O-carboxymethylchitosan of claim 1, or a pharmaceutically-acceptable salt thereof, to tissue under conditions such that post-surgical adhesions are minimized.

34. Intermolecularly bridged N,O-carboxymethylchitosan, wherein bridging occurs through an amide linkage between a carboxyl group of a first N,O-carboxymethylchitosan chain and a carboxyl group of a second N,O-carboxymethylchitosan chain.

35. Intermolecularly bridged N,O-carboxymethylchitosan, wherein bridging occurs through an amide linkage between amino groups on first and second N,O-carboxymethylchitosan chains, wherein said amino groups are linked by a bridging moiety.

* * * * *